United States Patent
Yelick et al.

(10) Patent No.: US 11,504,303 B2
(45) Date of Patent: *Nov. 22, 2022

(54) PULP REGENERATION COMPOSITIONS AND METHODS OF FORMING AND USING THE SAME

(71) Applicants: TRUSTEES OF TUFTS COLLEGE, Medford, MA (US); THE BRIGHAM AND WOMEN'S HOSPITAL, INC., Cambridge, MA (US)

(72) Inventors: Pamela C. Yelick, Boston, MA (US); Ali Khademhosseini, Cambridge, MA (US)

(73) Assignees: TRUSTEES OF TUFTS COLLEGE, Medford, MA (US); THE BRIGHAM AND WOMEN'S HOSPITAL, INC., Cambridge, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 17/557,483

(22) Filed: Dec. 21, 2021

(65) Prior Publication Data
US 2022/0110836 A1  Apr. 14, 2022

Related U.S. Application Data

(63) Continuation of application No. 15/777,304, filed as application No. PCT/US2017/064312 on Dec. 1, 2017, now Pat. No. 11,278,474.

(60) Provisional application No. 62/428,870, filed on Dec. 1, 2016.

(51) Int. Cl.
A61K 6/62 (2020.01)
A61C 5/40 (2017.01)
A61K 6/56 (2020.01)

(52) U.S. Cl.
CPC .................. *A61K 6/62* (2020.01); *A61C 5/40* (2017.02); *A61K 6/56* (2020.01)

(58) Field of Classification Search
CPC ....................................................... A61K 6/62
See application file for complete search history.

(56) References Cited

U.S. PATENT DOCUMENTS

2013/0217123 A1  8/2013  Giovent
2015/0274805 A1  10/2015  Annabi
2016/0296664 A1* 10/2016  Lu .................... A61K 9/0024

OTHER PUBLICATIONS

International Search Report from International Application No. PCT/US2017/064312 dated Feb. 13, 2016.
Khayat, "Pulp Regeneration in Different Prospective," A Thesis Presented to the Faculty of Tufts University School of Dental Medicine, Jun. 2016, pp. 50-70.
Chen et al., "Fabrication of Gelatin Methacrylate/Nanohydroxyapatite Microgel Arrays for Periodontal Tissue Regeneration," International Journal of Nanomedicine, vol. 11, pp. 4707-4718, Sep. 14, 2016.

(Continued)

*Primary Examiner* — Michael F Pepitone
(74) *Attorney, Agent, or Firm* — Nixon Peabody LLP

(57) ABSTRACT

A dental tissue regenerative composition. The composition includes a combination of (1) human dental pulp stem cells and (2) at least one of human umbilical vein endothelial cells or vascular endothelial growth factor. The combination is encapsulated in a light-activated gelatin methacrylate hydrogel.

27 Claims, 7 Drawing Sheets

(56) References Cited

OTHER PUBLICATIONS

Schneider et al., "White Mineral Trioxide Aggregate Induces Migration and Proliferation of Stem Cells from the Aplcal Papilla," Journal of Endodontics, vol. 40(7), PMC Jul. 1, 2015.

Dissanayaka et al., "The Interplay of Dental Pulp Stem Cells and Endothelial Cells in an Injectable Peptide Hydrogel on Angiogenesis and Pulp Regeneration In Vivo," Tissue Engineering: Part A, vol. 21, Nos. 3 and 4, 2015, pp. 550-563.

Nichol, J.W. et al., "Cell-laden microengineered gelatin methacrylate hydrogels," A. Biomaterials 2010, 31, 5536-5544.

Khayat et al., "GelMA-Encapsulated hDPSCs and HUVECs for Dental Pulp Regeneration," Journal of Dental Research 2017, vol. 96(2), pp. 192-199.

Klotz, B. J. et al., "Gelatin-Methacryloyl Hydrogels: Towards Biofabrication-Based Tissue Repair," Trends Biotechnol., 34(5): 394-407, May 2016.

Pradan, S. et al., "PEG-fibrinogen hydrogels for three-dimensional breast cancer cell culture," J. Biomed. Mater. Res. Part A, 105A(1): 236-252, Oct. 14, 2016.

\* cited by examiner

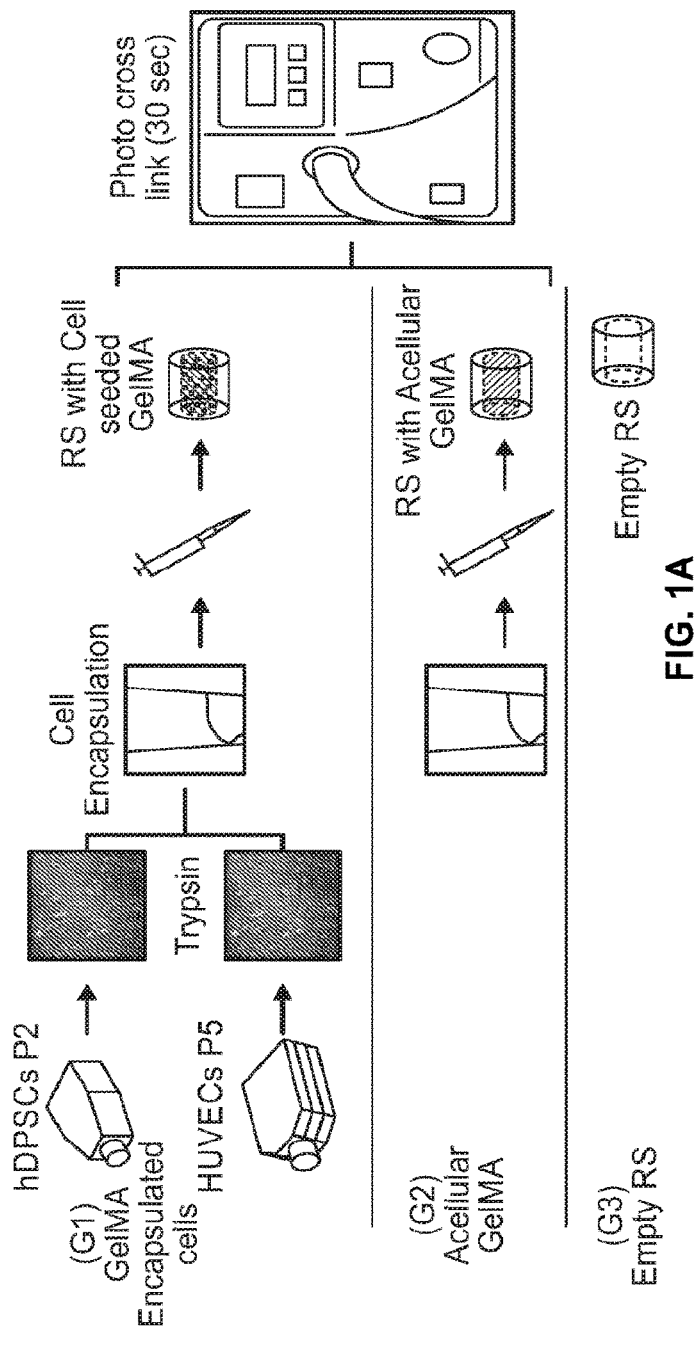
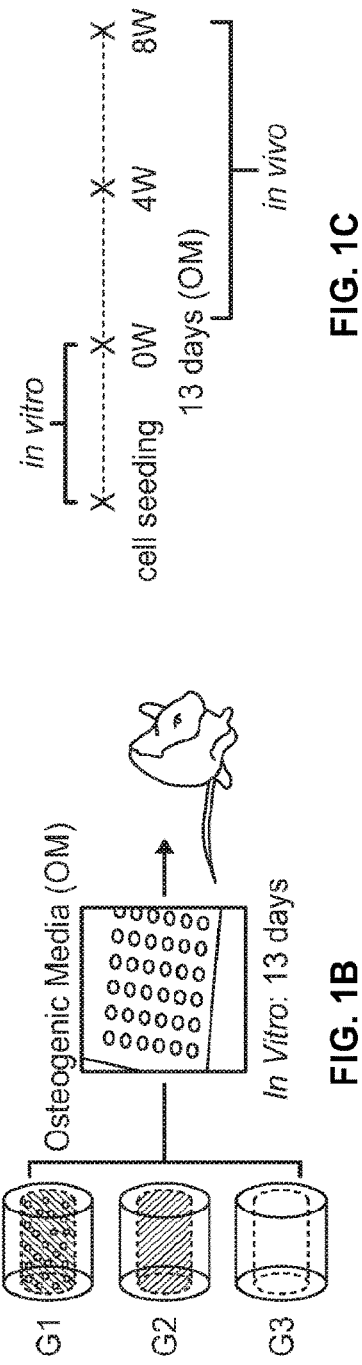
FIG. 1A
FIG. 1B
FIG. 1C

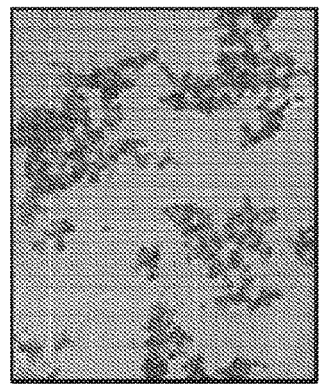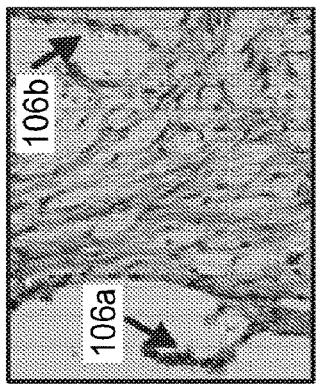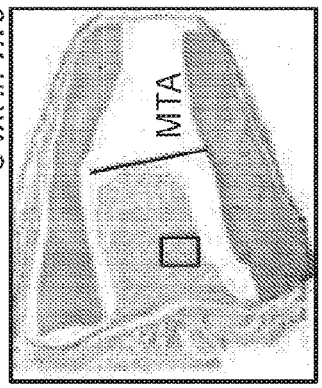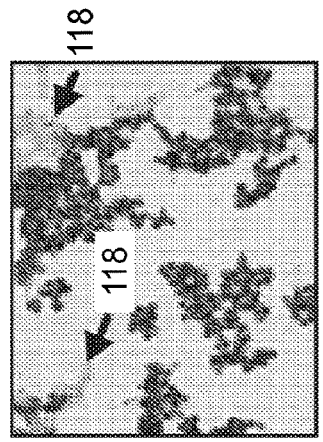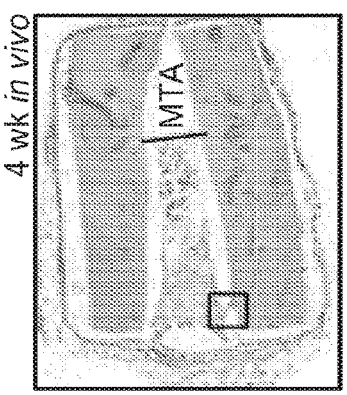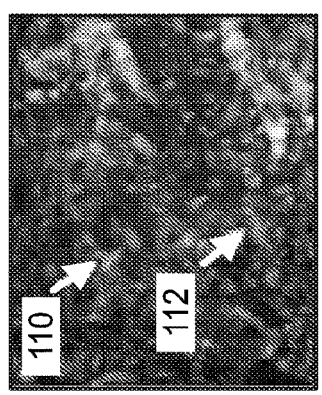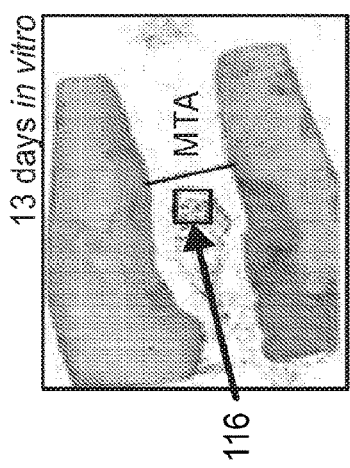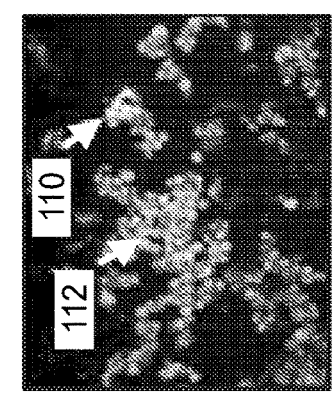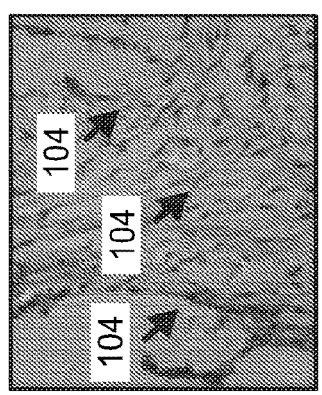

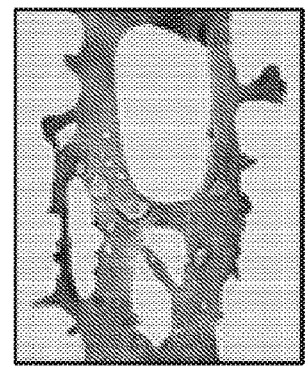
FIG. 3A
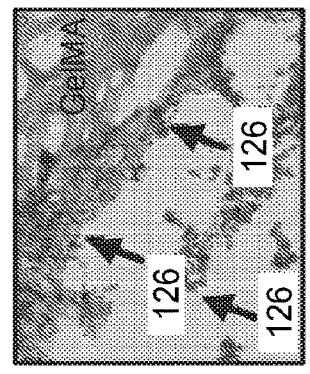
FIG. 3B
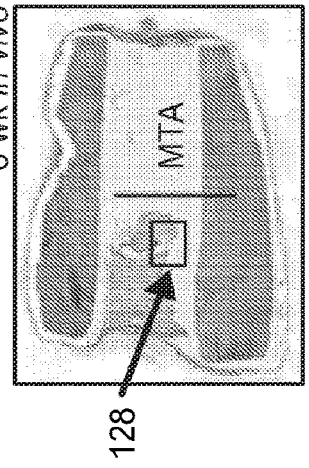
FIG. 3C
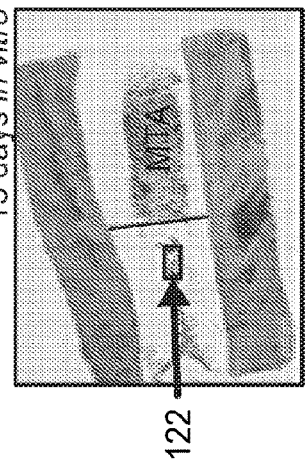
FIG. 3D
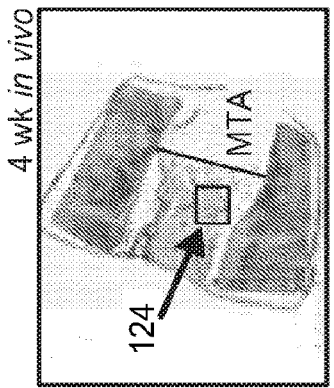
FIG. 3E
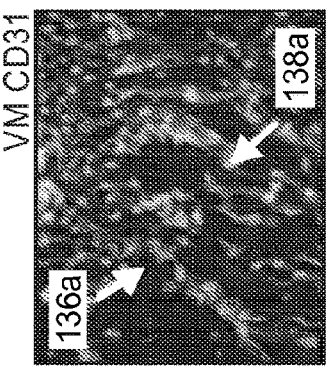
FIG. 3F
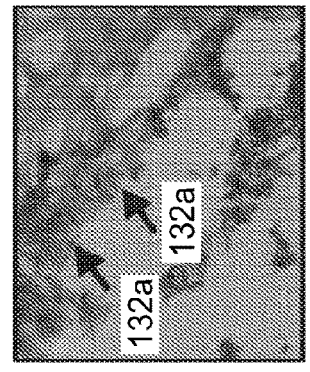
FIG. 3G
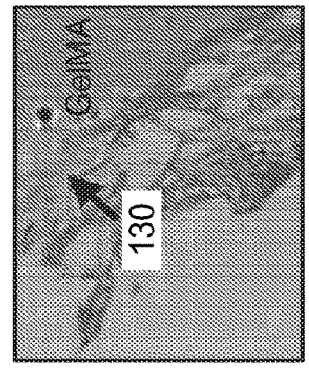
FIG. 3H
FIG. 3I <br>

<br>

<br>

<br>

<br>

<br>

<br>

PULP REGENERATION COMPOSITIONS AND METHODS OF FORMING AND USING THE SAME

CROSS-REFERENCE TO RELATED APPLICATION(S)

This application is a continuation of U.S. patent application Ser. No. 15/777,304, filed May 18, 2018, which is a U.S. National Stage of International Application No. PCT/US2017/064312, filed on Dec. 1, 2017, which claims priority to and benefit of U.S. Provisional Patent Application No. 62/428,870, filed Dec. 1, 2016, each of which are hereby incorporated by reference in their entireties.

GOVERNMENT SUPPORT

This invention was made with government support under grant no. R01DE016132(PCY), awarded by the National Institutes of Health, the National Institute of Dental and Craniofacial Research, and the National Institute of Biomedical Imaging and Bioengineering. The government has certain rights in the invention.

TECHNICAL FIELD

The present invention relates to compositions and methods for dental pulpal revascularization, replacing infected dental pulpal tissues in pulpotomy, or temporary intra canal dental medicaments. More specifically, the invention relates to compositions including human dental pulp stem cells, human umbilical vein endothelial cells, and/or vascular endothelial growth factor encapsulated in a light-activated gelatin methacrylate hydrogel and methods of forming and using the same.

BACKGROUND

Pulpal revascularization therapy is commonly used in dental clinics to obtain apical closure of immature permanent teeth with thin dentinal walls and/or on injured teeth to promote continued root development and to prevent fracture of thin dentinal walls. Goals of this therapy include achieving apical closure development similar to that of adjacent teeth, preventing tooth and supporting bone loss, and/or minimizing the need for and the financial burden associated with dental implant placement.

Regardless of these good intentions, undesirable outcomes can occur following clinical revascularization procedures. For example, stimulating bleeding from the periapical area of a tooth may deleteriously affect tooth root maturation. Other undesirable outcomes that may occur include arrested tooth root development, incomplete closure of the tooth apex, calcification within the pulpal space that may impede future root canal treatment, combinations thereof, or the like.

Induced bleeding at the tooth apex is a procedure used to activate the proliferation and migration of Stem Cells from Apical Papilla (SCAP) into the pulpal space and to release growth factors such as Platelet-Derived Growth Factor (PDGF), which participate in angiogenesis. Unfortunately, insufficient bleeding is commonly observed, leading to possible arrested tooth root development.

Several in vivo studies have attempted to regenerate the dentin-pulp complex by incorporating cells such as human Dental Pulp Stem Cells (hDPSCs), Human Umbilical Vein Endothelial Cells (HUVECs), and SCAP. These in vivo studies utilized scaffolds such as PURAMATRIX (3-D Matrix, Ltd, Tokyo, Japan), nanofibrous gelatin/silica bioactive glass (NF-gelatin/SBG) hybrid, Collagen, poly L lactic acid (PLLA), and Flouroapetite crystal coated with poly caprolactone. Others studies have demonstrated the ability to regenerate pulp-like tissue using scaffold-free approaches, including cell sheath technology and DSC aggregates formed on agarose dishes.

3D biomimetic tooth bud models have been created using photopolymerizable Gelatin Methacrylate (GelMA) hydrogel. These model were designed to facilitate dental epithelial (DE) and dental mesenchymal (DM) cell interactions leading to ameloblast and odontoblast differentiation, respectively, and the formation of bioengineered teeth of predictable size and shape.

GelMA hydrogels exhibit numerous properties that make them useful for a variety of tissue engineering applications. For example, GelMA is largely composed of denatured collagen and retains many of collagen's natural properties including RGD adhesive domains and MMP sensitive sites that enhance cell binding and cell-mediated matrix degradation. In addition, the physical properties of GelMA hydrogels can generally be tuned by varying GelMA and/or photo-initiator (PI) concentrations. GelMA is also suitable for cell encapsulation at about 37° C. and for promoting cell viability and proliferation. Further still, GelMA is relatively inexpensive.

GelMA formulas exhibiting elastic moduli similar to natural dental enamel and pulp organ tissues, respectively, have been identified. Such formulas have been found to be suitable for bioengineered tooth applications. Incorporating HUVECs along with DE and DM cells in bioengineered 3D GelMA tooth bud constructs was found to promote neovascular formation and facilitate in vivo engraftment with host vasculature.

hDPSCs have recently been considered for use in pulpal regeneration. DPSCs have been found to exhibit the potential to regenerate dentin-pulp complex after being seeded onto poly-D,L-lactide/glycolide scaffold and transplanted in vivo for about 3-4 months. However, existing challenges for this approach include identifying a scaffold that truly mimics the ECM of natural pulp and creating a sufficient blood supply to ensure the survival of in vivo transplanted DPSCs.

The below-described devices, methods, and systems address many of these deficiencies by using GelMA hydrogels and, specifically, GelMA encapsulated hDPSCs and HUVECs and/or vascular endothelial growth factor (VEGF) for clinically relevant applications for pulpal regeneration.

SUMMARY

According to aspects of the present disclosure, a dental tissue regenerative composition comprises a combination of (1) human dental pulp stem cells and (2) at least one of human umbilical vein endothelial cells or vascular endothelial growth factor. The combination is encapsulated in a light-activated gelatin methacrylate hydrogel. It is contemplated that other hydrogel scaffolds may also be used.

According to additional aspects of the present disclosure, a method of regenerating pulp-like tissues in a tooth root segment of a tooth includes injecting a composition into the tooth root segment. The composition includes gelatin methacrylate hydrogel and a photo-initiator. The method further includes combining the composition with a mixture of (1) human dental pulp stem cells and (2) at least one of human umbilical vein endothelial cells or vascular endothelial growth factor. The method further includes cross-linking the gelatin methacrylate hydrogel with the mixture by exposing the composition to a UV or visible light.

According to a further aspect of the present disclosure, a method of forming a dental tissue regenerative composition includes combining human dental pulp stem cells, at least one of human umbilical vein endothelial cells or vascular endothelial growth factor, a gelatin methacrylate hydrogel, and a photo-initiator. The method further includes crosslinking the gelatin methacrylate hydrogel with the human dental pulp stem cells and the at least one of human umbilical vein endothelial cells or vascular endothelial growth factor by exposure to a UV or visible light.

These and other capabilities of the inventions, along with the inventions themselves, will be more fully understood after a review of the following figures, detailed description, and claims.

BRIEF DESCRIPTION OF THE DRAWINGS

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention as defined by the appended claims.

FIG. 1A is a schematic diagram showing: GelMA-encapsulated cell constructs (G1) injected into human root segment (RS) and photocrosslinked for about 30 seconds; acellular GelMA RSs (G2) photocrosslinked for about 30 seconds; and empty RS (G3) that did not receive any treatment.

FIG. 1B is a schematic diagram illustrating that the 3 groups of FIG. 1A were cultured in osteogenic media (OM) and implanted subcutaneously.

FIG. 1C is a schematic timeline of the processes of FIGS. 1A and 1B.

FIG. 2A shows a sectioned G1 construct after about 13 day in vitro culture.

FIG. 2B shows an enlarged view of the boxed area of FIG. 2A.

FIG. 2C shows a polarized light microscopy (Pol) image of FIG. 2B.

FIG. 2D shows a double immunofluorescent (IF) image of the G1 construct of FIG. 2A.

FIG. 2E shows a sectioned G1 construct after about 4 weeks in vivo culture.

FIG. 2F shows an enlarged view of the boxed area of FIG. 2E.

FIG. 2G shows a Pol image of FIG. 2F.

FIG. 2H shows a double IF image of the G1 construct of FIG. 2E.

FIG. 2I shows a sectioned G1 construct after about 8 weeks in vivo culture.

FIG. 3A shows a sectioned G2 construct after about 13 days in vitro culture.

FIG. 3B shows an enlarged view of the boxed area of FIG. 3A.

FIG. 3C shows a Pol image of FIG. 3B.

FIG. 3D shows a sectioned G2 construct after about 4 weeks in vivo culture.

FIG. 3E shows an enlarged view of the boxed area of FIG. 3D.

FIG. 3F shows a Pol image of FIG. 3E.

FIG. 3G shows a double IF image of the G2 construct of FIG. 3D.

FIG. 3H shows a sectioned G2 construct after about 8 weeks in vivo culture.

FIG. 3I shows an enlarged view of the boxed area of FIG. 3H.

DETAILED DESCRIPTION

Figure 2L:
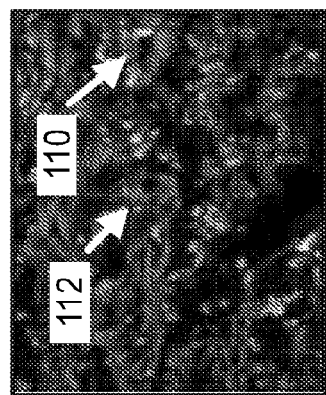
FIG. 2L shows a double IF image of the G1 construct of FIG. 2I.

While the inventions described herein are susceptible of embodiment in many different forms, there is shown in the drawings and will herein be described in detail preferred embodiments of the inventions with the understanding that the present disclosure is to be considered as an exemplification of the principles of the inventions and is not intended to limit the broad aspects of the inventions to the embodiments illustrated.

The embodiments described herein are directed to compositions and methods for regenerating pulp-like tissues in tooth root segments (RS) injected with human dental pulp stem cells (hDPSCs) and human umbilical vein endothelial cells (HUVECs) and/or vascular endothelial growth factor (VEGF) encapsulated in (e.g., 5% (w/v)) gelatin methacrylate (GelMA) hydrogel. It is contemplated that the GelMA may present at any suitable concentration including, but not limited to, about 3% to about 5% (w/v).

hDPSC may be isolated from dental pulp. In some embodiments, the dental pulp is from a mature tooth. The mature tooth may be a wisdom tooth, a cryopreserved tooth, or any other suitable mature tooth. In other embodiments, bleeding may be induced at or near the apex of the tooth to obtain hDPSCs from the blood.

According to one method, a dental tissue regenerative composition is formed. hDPSCs, at least one of HUVECs or VEGF, a GelMA hydrogel, and a photo-initiator are combined. The GelMA hydrogel is cross-linked with the hDPSCs and the at least one of HUVECs or VEGF by exposure to a UV or visible light.

According to another method, pulp-like tissues in a tooth root segment of a tooth are regenerated by injecting GelMA hydrogel and a photo-initiator into a tooth root segment. The GelMA hydrogel and the photo-initiator are combined with a mixture of (1) hDPSC and (2) at least one of HUVECs or VEGF, either before or after injection into the tooth root segment. The GelMA hydrogel is cross-linked with the mixture by exposing the composition to a UV or visible light. The cross-linking may be performed either prior to or after injection in the tooth root segment.

The duration of the exposure to the UV or visible light may range from about 15 seconds to about 35 seconds. In another embodiment, the exposure ranges from about 18 seconds to about 30 seconds.

To demonstrate the reliability of the compositions described herein, RS injected with acellular GelMA alone and empty RS were used as controls and compared with RS injected with hDPSCs and HUVECs encapsulated in about 5% GelMA hydrogel. Combined hDPSCs and HUVECs (in a ratio of about 1:1) were encapsulated in about 5% GelMA and injected into a RS orifice of about 6 mm length and about 2-3 mm wide. White mineral trioxide aggregate was used to seal one of the orifices while the other was left open. Samples were cultured in vitro in osteogenic media (OM) for about 13 days and subsequently implanted subcutaneously in nude rats for about 4 weeks and about 8 weeks. At least five sample replicates were used for each experimental group. The methods are described in more detail below.

Materials and Methods

Human Teeth Procurement, Dental Cell Isolation, and In Vitro Expansion

Human teeth extracted for clinically relevant reasons were obtained from the Tufts University School of Dental Medicine and the Back Bay Oral Maxillofacial Clinic in Boston, Mass. hDPSCs were isolated from dental pulp obtained from extracted wisdom teeth. HUVECs (PSC100010, ATCC, Manassas, Va.) were pre-cultured in vascular basal media (VBM) (PCS100030, ATCC) with vascular endothelial growth factor (VEGF) kit (PCS10004, ATCC) and humidified in about 5% $CO_2$ at about 37° C. Expanded cells were cryopreserved in about 10% dimethyl sulfoxide (DMSO) in appropriate culture media until use.

Cryopreserved Passage 2 hDPSCs were cultured in OM, including Dulbecco's Modified Eagle's medium (DMEM)/F12 supplemented with about 1% PSA, about 10% FBS, about 100 nM dexamethasone, about 10 mM beta glycerol phosphate, and about 0.05 mM ascorbic acid for about 13 days. Cryopreserved Passage 5 HUVECs were expanded in vitro in VBM with media changes about every 2 days.

Research Design

Three groups of root segments (RS) were examined in this study: (1) G1—GelMA encapsulated hDPSC/HUVEC filled RS; (2) G2—acellular GelMA filled RS; and (3) G3—empty RS. Replicate samples were cultured for about 13 days in OM in vitro. Five replicates of each group were fixed and analyzed using histological and immunohistochemical (IHC) methods. The remaining RSs were implanted subcutaneously in nude rats and grown for about 4 weeks and about 8 weeks (see FIGS. 1A-1C).

FIGS. 1A-1C illustrate a schematic of the design according to one embodiment. Specifically, GelMA encapsulated cell constructs (G1) consisting of cultured hDPSCs and HUVECs that were encapsulated in about 5% of GelMA, injected into human RS, and photocrosslinked for about 30 seconds. Acellular GelMA RSs (G2) were also photocrosslinked for about 30 seconds. Empty RS (G3) did not receive any treatment. FIG. 1B shows the 3 groups of FIG. 1A being cultured in OM for about 13 days and then implanted subcutaneously for about 4 weeks or about 8 weeks. FIG. 1C illustrates a schematic timeline of the processes of FIGS. 1A, 1B.

GelMA Preparation

Lyophilized GelMA was fully dissolved in DMEM/F12 media, and about 0.1% (w/v) of photo-initiator (PI) (Irgacure2959, Sigma, St. Louis, Mo.) was added to create about 5% GelMA solution (denoted as 5% GelMA), which was sterilized by filtration using a 0.22 µm filter and stored in the dark until use.

It is contemplated that the photo-initiator may be present at any suitable concentration including, but not limited to, about 0.05% to about 0.5% (w/v). In some embodiments, the concentration of the photo-initiator is about 0.1% (w/v). It is also contemplated that any suitable photo-initiator or combination of photo-initiators may be used. For example, the photo-initiator may include 1-[4-(2-hydroxyethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, or any combination thereof.

Tooth Root Section Selection Criteria, Disinfection, and MTA Placement

Teeth were collected from healthy patients aged about 15 to about 30 years old, including single and multi-rooted teeth with Type I & V Vertucci root canal configurations. Teeth containing caries, Type II-IV Vertucci root canal configuration, calcified canals, or those with prior root canal treatment were excluded. Tooth RSs were cut using sterilized 330 and fissure burs, from the coronal and middle third of the roots to minimize root curvature. RS were about 6 mm in length and of about 2-3 mm orifice width to facilitate injection of cellular and acellular GelMA. The pulpal space lumen was enlarged using Gates Glidden (GG) sizes 1 and 2 and the previously mentioned burs. Next, RSs were prepared using ethylenediaminetetraacetic acid (EDTA), Sodium hypochlorite (NaOCL), and phosphate buffered saline (PBS) washes. To test for any remaining microbial contamination, RS were cultured in DMEM/F12 media at about 37° C. for about 4 days. White Mineral Trioxide Aggregate (WMTA, ProRoot DENTSPLY Tulsa Dental Specialties, Tulsa, Okla.) was then used to create a plug at one side of each RS to mimic the clinical situation, while the other end was left open to allow host cell invasion.

Cell Preparation and GelMA Encapsulation

Confluent flasks of hDPSCs and HUVECs were trypsinized and resuspended in their respective media, and cell densities were calculated using a Countess Automated Cell Counter (Invitrogen™, Carlsbad, Calif.). A total of about $6 \times 10^5$ hDPSCs and about $6 \times 10^5$ HUVECs (in a ratio of about 1:1) were combined into one 50 ml tube and resuspended in about 0.5 mL of filtered about 5% GelMA. Approximately 30 µL of GelMA with hDPSCs and HUVECs (about $7.0 \times 10^4$ cells), or acellular GelMA, were injected into RSs and photocrosslinked via exposure to about 9.16 W/cm² UV light for about 20 seconds using an Omnicure 52000 (Lumen Dynamics Group Inc., Mississauga, ON, Canada).

Subcutaneous Implantation in Nude Rats

Using Tufts University approved IACUC Protocols, implants were placed in 8 female Nude rats aged about 4 weeks to about 6 weeks. Four incisions were created, two on each side, and fascia was separated from the muscle to form a lateral sac deep enough to hold an individual RS. After implantation, the incisions were closed with wound clips. The rats were checked every day for one week, and Buprenorphine was administered once every two days for one week.

Root Segment (RS) Harvest

Replicate RSs were harvested at about 4 weeks and about 8 weeks using TUSDM approved IACUC protocols, washed 3 times in PBS, fixed in about 10% Formalin overnight, washed with PBS, and decalcified in about 10% EDTA at a pH of about 7 for about 4 months. Decalcification was monitored by taking about 5 ml of the about 10% EDTA solution each week and adding a drop of about 1.0 M HCL plus about 1 ml of saturated Ammonium Oxalate. The solution was mixed thoroughly, allowed to sit for about 20 minutes, and monitored for $CaPO_4$ precipitate. Lack of precipitate formation was defined as substantially complete decalcification.

Cryosectioning

Samples were prepared for cryostat sectioning as previously described. Samples were wrapped in plastic wrap to prevent dehydration and stored at a temperature of about −80° C. A cryostat (Leica Biosystems, Nussloch, Germany) set at about −21° C. was used to section samples at about 10 μm or about 30 μm intervals, for histological/IF and confocal analyses, respectively. Magic Tape (Cryofilm Type2C, Section-Lab, Hiroshima, Japan) was used to transfer sections to Superfrost® Plus Microscope Slides Precleaned (Fisher Scientific, Atlanta, Ga.) and stored at about −20° C. until use.

Hematoxylin and Eosin (H&E) Stain

To avoid dislodging samples from Magic-Tape glass slides, the slides were carefully dipped three times in deionized water (DI $H_2O$) and stained with H&E stain using standard protocol. Dehydration was performed by dipping two or three times in about 95% ethanol (EtOH) and about 100% EtOH and one time in Xylene. Samples were cover slipped using Permount (Fisher Scientific, Atlanta, Ga.).

Double Immunofluorescent (IF) Histochemical Analyses

IF was performed as briefly described above. Primary antibodies included mouse α CD31 (1:200, ab187377, Abcam, Cambridge, Mass.) and rabbit α Vimentin (1:25, bs-0756R, Bioss, Woburn, Mass.). Secondary antibodies included goat α mouse (Invitrogen, 568, 1:50, West Grove, Pa.) and goat a Rabbit (Invitrogen, 488, 1:50, West Grove, Pa.). Mouse α rh-Mitochondria (1:25, Millipore Sigma, MAB1273, Temecula, Calif.) was used to discriminate between HUVEC and host endothelial cells.

Results

Analyses of harvested samples found that pulp-like tissues formed in hDPSC/HUVEC encapsulated GelMA-filled RS and that host cell infiltration was observed in the acellular GelMA and empty RS groups. hDPSCs and HUVECs were identified using IF histochemical analysis for Vimentin and CD31, respectively. Construct cells were distinguished from host cells using IF with an anti-rh-mitochondrial antibody.

(G1) GelMA Encapsulated Cell Tooth Root Segments

Figure 2K:
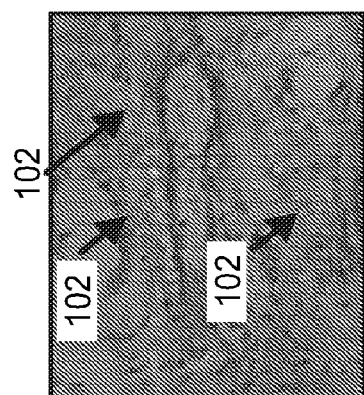
FIG. 2K shows a Pol image of FIG. 2J.
Figure 2J:
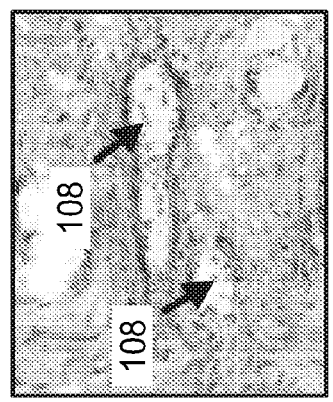
FIG. 2J shows an enlarged view of the boxed area of FIG. 2I.

Prior to encapsulation, in vitro cultured hDPSCs and HUVEC exhibited typical fibroblastic and cobblestone-like morphologies, respectively (not shown). G1 (GelMA encapsulated hDPSC/HUVEC RSs) exhibited cellularized bioengineered pulp-like tissue after about 13 days in vitro culture (see FIGS. 2A, 2B). Cellularity of the G1 constructs appeared to increase in about 4 week and about 8 week in vivo implanted constructs (see FIGS. 2E, 2F, 2I, 2J), to eventually occupy substantially all of the pulpal space not containing MTA. Polarized light imaging revealed collagen deposition 102, 104 in about 4 week and about 8 week in vivo implanted G1 samples. Collagen deposition 102 appeared more organized at about 8 weeks as compared to collagen deposition 104 at about 4 weeks (see FIGS. 2K and 2G). Neovascularization 106a, 106b was observed in about 4 week in vivo implanted samples (FIG. 2F). The 8 week G1 in vivo implants showed patent blood vessels containing red blood cells 108 (FIG. 2J). IF analyses of VM expressing 110 hDPSCs and CD31 expressing 112 HUVECs in G1 RSs revealed neovascular network formation over implantation time (see FIGS. 2D, 2H, 2L).

As briefly discussed above, FIGS. 2A-2L show GelMA encapsulated hDPSC/HUVEC RSs of G1. FIG. 2A shows a sectioned G1 construct after about 13 days in vitro culture. FIG. 2A shows bioengineered pulp and the location of MTA plug. FIG. 2B is an enlarged view of the boxed area 116 of FIG. 2A showing cellularity of construct and undegraded GelMA 118. As shown in FIG. 2C, polarized light (Pol) microscopy showed no or substantially no ECM deposition. FIG. 2D shows a double IF of CD31 expressing HUVECs 112 and VM expressing hDPSCs 110.

As shown in FIG. 2E, a sectioned 4 week in vivo implanted construct exhibited higher cell density and organization as compared to 13 days in vitro (see FIG. 2A). As shown in FIG. 2F, odontoblast-like cells 106a were present at the pulp-dentin interface, and functional neovascularization-containing red blood cells 106b were observed. As seen in FIG. 2G, Pol microscopy showed obvious ECM deposition 104 at about 4 weeks as compared to about 13 day in vitro cultured RS (see FIG. 2C). As shown in the double IF image of FIG. 2H, there was increased cellularity of both hDPSCs 110 and HUVECS 112.

FIG. 2I shows that about 8 week in vivo implanted G1 RSs exhibited high cellularity. As shown in FIG. 2J, implant vascularization 108 appeared more distinct as compared to about 4 week G1 implants (see FIG. 2F). As seen in FIG. 2K, increased collagen deposition 102 was apparent at about 8 weeks in vivo as compared to about 4 week in vivo implanted G1 samples (see FIG. 2G). Double IF revealed high cellularity of hDPSCs and HUVECS. The scale bars of FIGS. 2A-2K were as follows: FIGS. 2A, 2E, 2I=500 μm; FIGS. 2B, 2C, 2F, 2G, 2J, 2K=20 μm; and FIGS. 2D, 2H, 2L=50 μm. 127×70 mm (300×300 DPI).

(G2) Acellular GelMA-Filled Tooth Root Segments

G2, Acellular GelMA RSs were found to exhibit degraded GelMA after about 13 day in vitro culture (see FIG. 3A, B). FIG. 3A shows that sectioned 13 day in vitro cultures of acellular RS exhibited degraded GelMA and remnant MTA. FIG. 3B is an enlarged view of the boxed area 122 of FIG. 3A and shows remnant GelMA. As shown in FIG. 3C, polarized light imaging did not detect organized collagen. In about 4 week (FIGS. 3D, 3E) and about 8 week (FIGS. 3H, 3I) in vivo implanted G2 constructs, host cells were present on both the GelMA and dentin surfaces, and host cell density appeared to increase over in vivo implantation time. As shown in FIG. 3D, about 4 week in vivo G2 implants exhibited increased cellularity as compared to 13 days in vitro cultured G2 constructs (see FIG. 3A). The area 124 in FIG. 3D (enlarged in FIG. 3E) shows host cellularity, attachment to GelMA, and vascularity including host red blood cells 126.

Figure 3K:
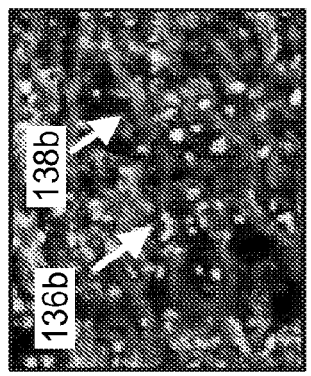
FIG. 3K shows a double IF image of the G2 construct of FIG. 3H.
Figure 3J:
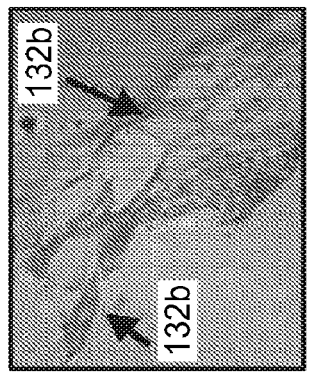
FIG. 3J shows a Pol image of FIG. 3I.
Figure 4C:
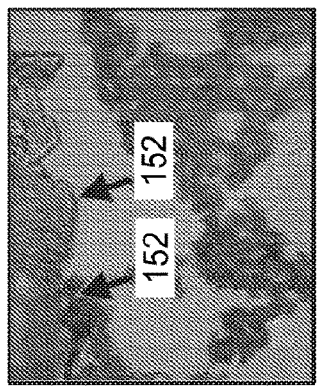
FIG. 4C shows a Pol image of FIG. 4B.
Figure 4F:
FIG. 4F shows an enlarged view of the boxed area of FIG. 4E.

As shown in FIG. 3H, sectioned about 8 week in vivo implants revealed high cellularity and invading host cells. The boxed area 128 in FIG. 3H (enlarged in FIG. 3I) revealed generally undegraded GelMA that persisted in about 8 week in vivo implanted G2 constructs and host cells 130. Generally undegraded GelMA was detectable in both about 4 week (FIG. 3E) and about 8 week (FIG. 3I) in vivo implanted constructs. Red blood cells 126, 130 were observed in acellular GelMA RS (see FIGS. 3E and 3I). Polarized light microscopy revealed host cell collagen deposition 132 in about 4 week and about 8 week in vivo implanted G2 constructs (see FIG. 3F, 3J). As shown in FIG. 3F, polarized light revealed host cell derived ECM 132a. As shown in FIG. 3J, polarized light microscopy revealed increased host derived ECM deposition 132b as compared to about 4 week in vivo implanted G2 constructs (FIG. 4F).

Double IF revealed VM-expressing host mesenchymal stem cells (MSCs) 136 and CD31-expressing host endothelial cells 138 in about 4 week (FIG. 3G) and 8 week (FIG. 3K) in vivo implanted G2 constructs. As shown in FIG. 3G, double IF revealed host CD31-expressing endothelial 138a and Vimentin-expressing mesenchymal cells 136a. As shown in FIG. 3K, double IF revealed CD31-expressing host endothelial cells 138b and VM-expressing host mesenchymal cells 136b in about 8 week in vivo implanted G2 constructs. The scale bars used in FIGS. 3A-3K are as follows: FIGS. 3A, 3D, 3H=500 μm; FIGS. 3B, 3C, 3E, 3F, 3I, 3J=20 μm; and FIGS. 3G, 3K=50 μm. 127×70 mm (300×300 DPI).

(G3) Empty Tooth Root Segments

Figure 4B:
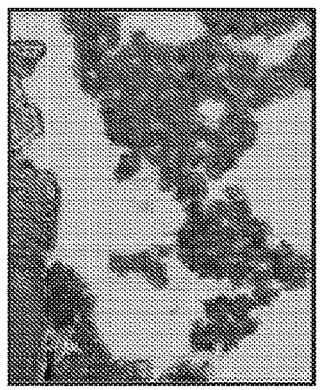
FIG. 4B shows an enlarged view of the boxed area of FIG. 4A.

In vivo implanted G3, empty RSs, also exhibited host cell infiltration at about 4 weeks and about 8 weeks (FIGS. 4A, 4B and FIGS. 4E, 4F, respectively). A shown in FIG. 4A, G3 constructs at about 4 weeks in vivo implantation showed host encapsulation and cellularity within the pulpal space. As shown in FIG. 4B (the enlarged view of boxed area 148 of FIG. 4A), host cells attached to the dentin surface, and host cells infiltrated into the pulpal space.

Figure 4E:
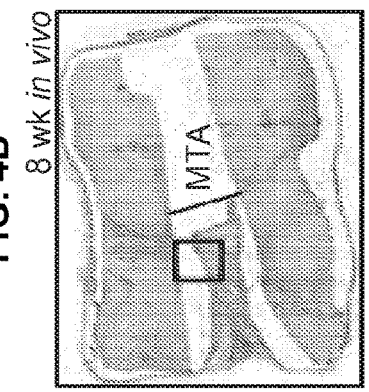
FIG. 4E shows a sectioned G3 construct after about 8 weeks in vivo culture.
Figure 4H:
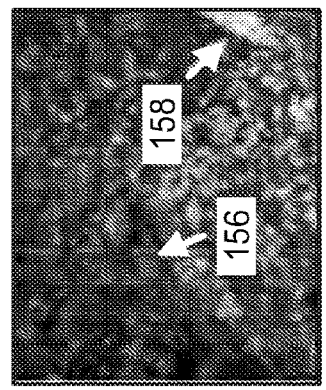
FIG. 4H shows a double IF image of the G3 of FIG. 4E.
Figure 4A:
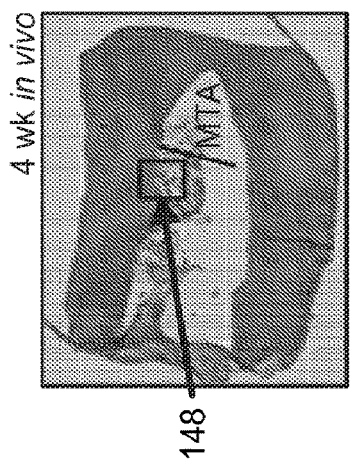
FIG. 4A shows a sectioned G3 construct after about 4 weeks in vivo culture.
Figure 4D:
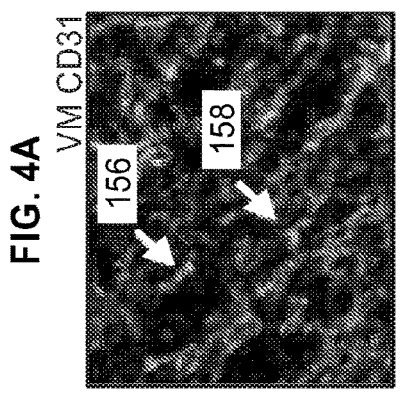
FIG. 4D shows a double IF image of the G3 construct of FIG. 4A.
Figure 4G:
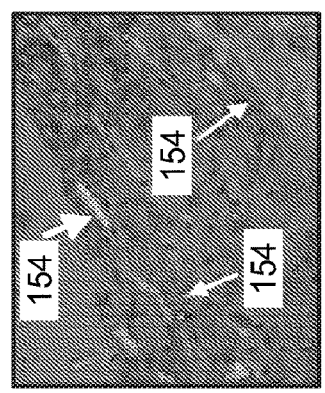
FIG. 4G shows a Pol image of FIG. 4F.

As shown in FIG. 4E, about 8 week in vivo implanted G3 constructs exhibited increased cellularity as compared to about 4 week G3 implants (see FIG. 4A). As shown in FIG. 4F, more distinct host cellularity was observed in about 8 week as compared to about 4 week in vivo implanted G3 samples (see FIG. 4B). Host cell-derived ECM in implanted G3 constructs appeared more organized at about 8 weeks (see FIG. 4G) as compared to about 4 weeks (see FIG. 4C), as revealed by polarized light microscopy. As shown in FIG. 4G, polarized light imaging revealed increased host ECM deposition 154 at about 8 weeks as compared to about 4 weeks (see FIG. 4C) in vivo implantation. As shown in FIG. 4C, polarized light revealed dentin ECM 152 only. IF histochemical analyses revealed CD31 positive host vascularity 158 and VM-expressing MSCs 156 in in vivo implanted empty RSs (see FIGS. 4D, 4H). As shown in FIG. 4D, double IF revealed the presence of host endothelial and mesenchymal tissues. Double IF showed similar results in the about 8 week in vivo implanted G3 constructs (FIG. 4H) as the about 4 week in vivo implanted G3 constructs (FIG. 4D). Neovasculature of empty RSs appeared less organized than that present in acellular GelMA RSs and much less than was observed in in vivo implanted hDPSC/HUVEC encapsulated GelMA RSs. The scale bars of FIGS. 4A-4H are as follows: FIGS. 4A, 4E=500 μm; FIGS. 4B, 4C, 4F, 4G=20 μm; and FIGS. 4D, 4H=50 μm. 127×48 mm (300×300 DPI).

Discriminating Between Human and Host Cells

Figure 5B:
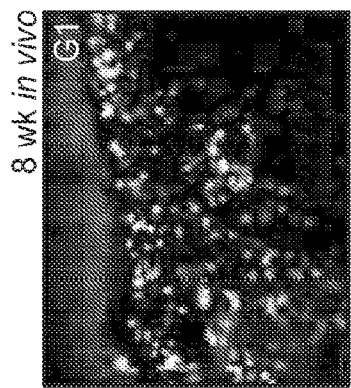
FIG. 5B illustrates that DPSCs and HUVECs in about 4 weeks in vivo implanted G1 constructs.
Figure 5C:
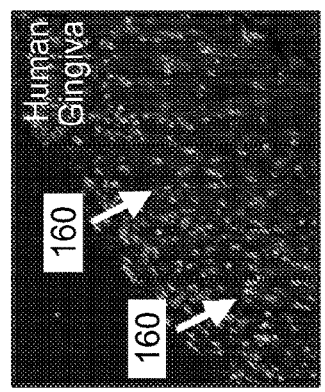
FIG. 5C illustrates a weak signal in about 8 weeks in vivo implanted constructs.
Figure 5A:
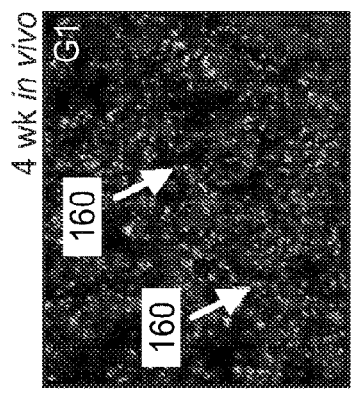
FIG. 5A shows Robust rh-Mitochondria staining of GelMA encapsulated hDPSCs and HUVECs at about 13 days in vitro.
Figure 5D:
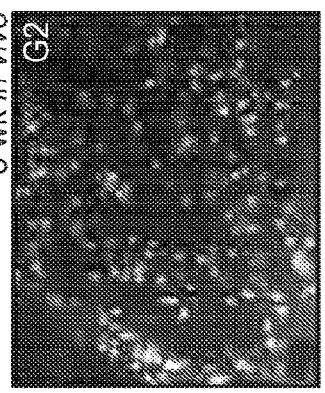
FIG. 5D illustrates rh-Mitochondria antibody identified human DPSC and HUVECs in about 4 weeks in vivo acellular GelMA implants.
Figure 5E:
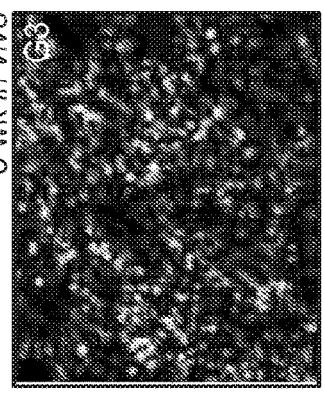
FIG. 5E illustrates rh-Mitochondria antibody identified human DPSC and HUVECs in about 8 weeks in vivo acellular GelMA implants.
Figure 5F:
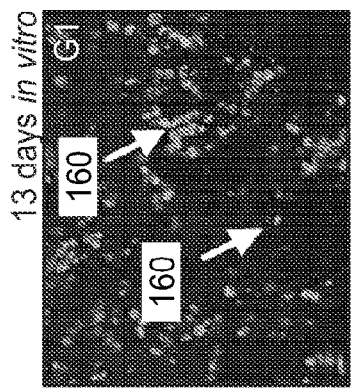
FIG. 5F illustrates a human gingiva positive control for the rh-Mitochondria antibody.
Figure 5G:
FIG. 5G illustrates about 4 weeks in vivo empty RS implants.
Figure 5H:
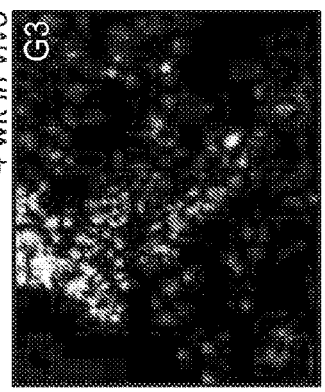
FIG. 5H illustrates about 8 weeks in vivo empty RS implants.

To evaluate the long-term survival of GelMA-encapsulated hDPSC and HUVEC cells and to discriminate between human and host cells, sectioned samples were examined using an anti-rh-mitochondria antibody that recognizes human cells and does not cross-react with rat cells. Human cells 160 were identifiable in G1 constructs after about 13 days in vitro culture and after about 4 weeks in vivo implantation (see FIGS. 5A, 5B) but not at about 8 weeks (see FIG. 5C) in vivo. In FIG. 5A, robust rh-Mitochondria staining of GelMA encapsulated hDPSCs and HUVECs at 13 days in vitro is shown. As shown in FIG. 5B, human DPSCs and HUVECs were also clearly detected in about 4 week in vivo implanted G1 constructs. As shown in FIG. 5C, weak signal in about 8 week implanted constructs indicated that implanted human cells were replaced by host cells. Acellular GelMA and empty RSs generally exhibited no positive rh-mitochondria expression (see FIGS. 5D, 5E, 5G, 5H). Positive control human gingiva was positive for rh-mitochondria (see FIG. 5F). As shown in FIGS. 5D, 5E, rh-Mitochondria antibody identified human DPSC and HUVECs in about 4 week and about 8 week in vivo acellular GelMA implants. As shown in FIGS. 5G and 5H, about 4 week and about 8 week in vivo empty RS implants exhibited similar results as the acellular GelMA group of FIGS. 5D, 5E. Namely, both groups exhibited host cell infiltration and no rh-Mitochondrial marker expression. FIG. 5F shows human gingiva positive control for the rh-Mitochondria antibody. The scale bars of FIGS. 5A-5H are as follows: 50 μm. 127×95 mm (300×300 DPI).

Discussion

One of the goals of the embodiments described herein was to define a more effective, clinically relevant method for pulpal revascularization and regeneration in human tooth root segments. First, hDPSCs were used in combination with HUVECs, based on the importance of both cell types for pulpal tissue formation and vascularity and on the successful use of HUVEC-derived neovasculature to facilitate implant viability and integration with host vasculature in in vivo implants. Moreover, it was reported that DPSCs contributed to increased neovascular network formation by facilitating HUVEC migration and by increasing vascular endothelial growth factor (VEGF) expression.

As discussed above, hDPSCs and HUVECs (and/or, in some embodiments, vascular endothelial growth factor (VEGF)) were encapsulated in GelMA, a preferred hydrogel scaffold for 3D tissue engineering applications based on its ability to facilitate cell attachment, spreading, proliferation, and promotion of host cell interactions. The ability to easily inject and photo-crosslink GelMA-encapsulated cells also makes GelMA an attractive scaffold for clinically relevant pulpal regeneration procedures. It is contemplated, however, that other hydrogel scaffolds may also or alternatively be used.

It is contemplated that the compositions described herein may be injected into a tooth root segment using any suitable device or method. In one non-limiting embodiment, a double barrel syringe may be used, in which the first barrel may include a photo-initiator and the second barrel may include GelMA. The contents of the first and second barrels may be simultaneously injected into the tooth root segment, or they may be injected in sequence.

Dental and endothelial cell-encapsulated GelMA may be used as constructs for 3D biomimetic tooth bud models. In such embodiments, GelMA formulas generally support DE and DM cell attachment, spreading, metabolic activity, and neo-vasculature formation by co-seeded endothelial cells (HUVECs). Selected GelMA formulas were used to create 3D tooth buds consisting of a biomimetic enamel organ layer (DE and HUVECs encapsulated in about 3% GelMA) and a biomimetic pulp organ (DM and HUVECs encapsulated in about 5% GelMA). The resultant 3D biomimetic tooth bud generally supported dental cell differentiation, vascularization, and in vivo formation of mineralized osteodentin tissues of specified size and shape. In the embodiments described herein, GelMA is used to create a biomimetic pulp organ containing both hDPSC and HUVECs encapsulated in about 5% GelMA, created in human tooth RSs, to study pulp regeneration.

H&E staining and polarized light (Pol) microscopy revealed that GelMA encapsulated hDPSC and HUVECs contributed to the formation of bioengineered pulp-like tissue that exhibited increased cellularity over in vivo implantation time (see FIG. 2). These data also showed that GelMA scaffold in G1 (cell-seeded) constructs had largely degraded after about 8 week in vivo implantation but was still detectable in G2 (acellular GelMA RSs) after about 8 weeks. Tight association of host tissues to the GelMA scaffold (which is generally indicative of good biocompatibility) and over the inner dentin surface of implanted RSs was observed (see FIGS. 3, 4). Additionally, acellular GelMA appeared to promote host tissue infiltration, proliferation, and vascularization of the implant (see FIG. 3).

Within each RS, WMTA was used to seal off one end of each RS to mimic clinical treatment of a natural tooth. Remnant MTA is clearly identifiable in some sectioned implants, although it appeared to have been lost from others during sample processing. Reparative dentin formation below the MTA was generally not observed, possibly due to the relatively short duration (1-2 months).

As discussed above, GelMA supported dental and HUVEC cell proliferation. It is noteworthy that host cell-derived ECM elaborated in G2 (acellular RSs) appeared somewhat more organized than that formed in G3 (empty RSs) after about 4 weeks and about 8 weeks in vivo implantation. Thus, GelMA may facilitate host cell infiltration and organization prior to degradation.

As described above, a functional vascularized network is required for the long term survival of bioengineered tissues and for proper integration with the recipient host. In natural tissues, blood vessels are composed of a luminal endothelial cell layer, surrounded by a layer of smooth muscle cells. Mesenchymal stem cells (MSCs) and endothelial cells have been shown to exhibit the ability to self-organize into capillary-like networks after encapsulation in GelMA hydrogel in vitro and in vivo. Confocal analyses and immunofluorescent (IF) histochemical analyses were used in the embodiments discussed herein to examine neo-vessel formation and organization within in vitro cultured and in vivo implanted samples. Elaborate neo-vascular and capillary-like network formation were identified in all in vivo implanted groups after about 4 weeks and about 8 weeks. However, more organized neovasculature networks were observed in G1 (GelMA-encapsulated hDPSC/HUVEC RSs) as compared to acellular and empty RSs. Importantly, the presence of host red blood cells within the bioengineered vasculature confirmed the ability of G1 constructs to form functional vascular networks in vivo, as would be required to support tooth integration and growth after implantation.

IF analyses using rh-mitochondria showed that the GelMA encapsulated hDPSCs and HUVECs survived for about 4 weeks in vivo implantation, but were generally not detectable at about 8 weeks in vivo (see FIG. 5C).

In conclusion, GelMA hydrogels may be used to support the formation of hDPSC/HUVEC derived, highly cellularized and vascularized pulp-like tissue formation in human tooth root segments and, to a lesser degree, in acellular GelMA constructs. GelMA may also support hDPSC/HUVEC cell attachment and proliferation and attachment for host cells. Cell-seeded GelMA hydrogels promote the establishment of host vasculature within the segments and promote extracellular matrix (ECM) deposition. These results validate GelMA encapsulated human cell constructs as a promising alternative therapy for clinically relevant pulpal revascularization, to replace infected pulpal tissues in pulpotomy procedures, and/or as a temporary intracanal medicament.

Although the embodiments described herein generally include human umbilical vein endothelial cells (HUVECs), it is contemplated that vascular endothelial growth factor (VEGV) may be used instead of or in addition to the HUVECs.

While the embodiments herein have been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention. It is also contemplated that additional embodiments according to aspects of the present invention may combine any number of features from any of the embodiments described herein.

What is claimed is:

1. A dental tissue regenerative composition comprising:
   a material at least partly obtained from an extracted tooth; and
   a light-activated gelatin methacrylate hydrogel encapsulating the material.

2. The composition of claim 1, further comprising a photo-initiator.

3. The composition of claim 2, wherein the photo-initiator is present at a concentration of about 0.05% to about 0.5% (w/v).

4. The composition of claim 1, wherein the photo-initiator is selected from the group consisting of: 1-[4-(2-hydroxyethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, and any combination thereof.

5. The composition of claim 1, wherein the gelatin methacrylate hydrogel is present at a concentration of about 3% to about 5% (w/v).

6. The composition of claim 1, wherein the material obtained from the extracted tooth includes dental pulp stem cells.

7. The composition of claim 6, wherein the material further includes at least one of umbilical vein endothelial cells or vascular endothelial growth factor.

8. The composition of claim 6, wherein the dental pulp stem cells have been isolated from dental pulp.

9. The composition of claim 8, wherein the dental pulp is from a mature tooth.

10. The composition of claim 1, wherein the composition is configured to be used for pulpal revascularization, to replace infected pulpal tissues in pulpotomy, as a temporary intra canal medicament, or for regenerating pulp-like tissues in tooth root segments.

11. A method of regenerating pulp-like tissues in a tooth root segment of a tooth, the method comprising:
   providing a composition comprising
      a gelatin methacrylate hydrogel,
      a photo-initiator, and
      a material at least partly obtained from an extracted tooth, the gelatin methacrylate hydrogel and the material having been cross-linked by exposure to a UV or visible light; and
   injecting the composition into the tooth root segment.

12. The method of claim 11, wherein the photo-initiator is present in the composition at a concentration of about 0.05% to about 0.5% (w/v).

13. The method of claim 11, wherein the photo-initiator is selected from the group consisting of: 1-[4-(2-hydroxy-ethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, and any combination thereof.

14. The method of claim 11, wherein the gelatin methacrylate hydrogel is present in the composition at a concentration of about 3% to about 5% (w/v).

15. The method of claim 11, wherein the material obtained from the extracted tooth includes dental pulp stem cells.

16. The method of claim 15, wherein the material further comprises at least one of umbilical vein endothelial cells or vascular endothelial growth factor.

17. The method of claim 15, wherein the dental pulp stem cells have been isolated from dental pulp.

18. The method of claim 17, wherein the dental pulp is from a mature tooth.

19. A method of forming a dental tissue regenerative composition, the method comprising:
   combining a material at least partly obtained from an extracted tooth, a gelatin methacrylate hydrogel, and a photo-initiator; and
   cross-linking the gelatin methacrylate hydrogel with the material by exposure to a UV or visible light.

20. The method of claim 19, wherein the photo-initiator is present at a concentration of about 0.05% to about 0.5% (w/v).

21. The method of claim 19, wherein the photo-initiator is selected from the group consisting of: 1-[4-(2-hydroxy-ethoxy)-phenyl]-2-hydroxy-2-methyl-1-propane-1-one, azobisisobutyronitrile, benzoyl peroxide, di-tert-butyl peroxide, 2,2-dimethoxy-2-phenylacetophenone, Eosin Y, and any combination thereof.

22. The method of claim 19, wherein the gelatin methacrylate hydrogel is present at a concentration of about 3% to about 5% (w/v).

23. The method of claim 19, wherein the material obtained from the extracted tooth includes dental pulp stem cells.

24. The method of claim 23, wherein the material further comprises at least one of umbilical vein endothelial cells or vascular endothelial growth factor.

25. The method of claim 23, wherein the dental pulp stem cells have been isolated from dental pulp.

26. The method of claim 25, wherein the dental pulp is from a mature tooth.

27. The method of claim 19, wherein the composition is configured to be used for pulpal revascularization, to replace infected pulpal tissues in pulpotomy, as a temporary intra canal medicament or for regenerating pulp-like tissues in tooth root segments.

* * * * *